(12) United States Patent
Kossarian

(10) Patent No.: US 11,238,224 B2
(45) Date of Patent: Feb. 1, 2022

(54) PERFORMING CHEMICAL TEXTUAL ANALYSIS

(71) Applicant: International Business Machines Corporation, Armonk, NY (US)

(72) Inventor: Malous M. Kossarian, San Mateo, CA (US)

(73) Assignee: International Business Machines Corporation, Armonk, NY (US)

( * ) Notice: Subject to any disclaimer, the term of this patent is extended or adjusted under 35 U.S.C. 154(b) by 993 days.

(21) Appl. No.: 15/793,897

(22) Filed: Oct. 25, 2017

(65) Prior Publication Data

US 2018/0046932 A1 Feb. 15, 2018

Related U.S. Application Data

(63) Continuation of application No. 15/237,466, filed on Aug. 15, 2016, now Pat. No. 10,679,004.

(51) Int. Cl.
| | |
|---|---|
| G06F 40/279 | (2020.01) |
| G16C 20/10 | (2019.01) |
| G16C 20/70 | (2019.01) |
| G06F 40/111 | (2020.01) |
| G16C 20/90 | (2019.01) |

(52) U.S. Cl.
CPC .......... *G06F 40/279* (2020.01); *G06F 40/111* (2020.01); *G16C 20/10* (2019.02); *G16C 20/70* (2019.02); *G16C 20/90* (2019.02)

(58) Field of Classification Search
CPC ...... G06N 7/005; G16C 20/10; G06F 17/2705
USPC .................................................. 706/15, 45
See application file for complete search history.

(56) References Cited

U.S. PATENT DOCUMENTS

| | | | |
|---|---|---|---|
| 7,243,112 B2 | 7/2007 | Qu et al. | |
| 8,793,073 B2 | 7/2014 | Chen et al. | |
| 10,262,107 B1* | 4/2019 | Tran | G06F 19/3475 |
| 10,679,004 B2 | 6/2020 | Kossarian | |
| 2002/0077757 A1* | 6/2002 | Bunin | G16C 20/90 |
| | | | 702/32 |
| 2005/0246316 A1* | 11/2005 | Lawson | G16C 20/70 |
| 2009/0094059 A1* | 4/2009 | Coleman | G16H 20/10 |
| | | | 705/3 |
| 2013/0179091 A1* | 7/2013 | Jackson | G16H 50/50 |
| | | | 702/30 |
| 2013/0185644 A1 | 7/2013 | Kitano et al. | |
| 2013/0218878 A1* | 8/2013 | Smith | G16C 20/80 |
| | | | 707/723 |
| 2015/0220680 A1* | 8/2015 | Boyer | G16B 5/00 |
| | | | 703/11 |
| 2016/0092793 A1* | 3/2016 | Garrow | G06N 20/10 |
| | | | 706/12 |

(Continued)

OTHER PUBLICATIONS

Notice of Allowance from U.S. Appl. No. 15/237,466, dated Feb. 6, 2020.

(Continued)

*Primary Examiner* — David R Vincent
(74) *Attorney, Agent, or Firm* — Zilka-Kotab, P.C.

(57) ABSTRACT

A computer-implemented method according to one embodiment includes identifying a textual document, determining chemical data within the textual document, performing an analysis of the chemical data to identify a chemical pathway, and calculating a probability score for the chemical pathway.

9 Claims, 6 Drawing Sheets

(56) References Cited

U.S. PATENT DOCUMENTS

2018/0046930 A1    2/2018  Kossarian
2018/0172667 A1*   6/2018  Noskov ................. G16B 15/00
2020/0234006 A1    7/2020  Kossarian

OTHER PUBLICATIONS

Non-Final Office Action from U.S. Appl. No. 15/237,466, dated Oct. 16, 2019.
Gene Ontology Consortium, Retrieved From http://geneontology.org/ on Aug. 15, 2016.
Kossarian, M., U.S. Appl. No. 15/237,466, filed Aug. 15, 2016.
Eisen et al., "Cluster analysis and display of genome-wide expression patterns," Proceedings of the National Academy of Sciences, Genetics, vol. 95, Dec. 1998 pp. 14863-14868.
Karp, P., "An ontology for biological function based on molecular interactions," Bioinformatics Ontology, vol. 16, No. 3, 2000, pp. 269-285.
Pensak et al., "LHASA-Logic and Heuristics Applied to Synthetic Analysis," ACS Symposium Series, American Chemical Society, Jun. 1, 1977, pp. 1-32.
Landrum, G., "RDKit Documentation," Release Sep. 1, 2016, Nov. 23, 2016, pp. 1-115.
Corey et al., "Computer-Assisted Synthetic Analysis for Complex Molecules. Methods and Procedures for Machine Generation of Synthetic Intermediates," Journal of the American Chemical Society, vol. 94:2, Jan. 26, 1972, pp. 440-459.
Kossarian, M., U.S. Appl. No. 16/842,587, filed Apr. 7, 2020.
List of IBM Patents or Patent Applications Treated as Related.

* cited by examiner

PERFORMING CHEMICAL TEXTUAL ANALYSIS

BACKGROUND

The present invention relates to textual analysis, and more specifically, this invention relates to performing textual analysis from a chemical perspective.

The analysis of chemical components and reactions is a major component of chemical development. However, physical chemical experimentation in a wet lab is time and resource intensive, as well as potentially hazardous. There is therefore a need to minimize undue experimentation.

SUMMARY

A computer-implemented method according to one embodiment includes identifying a textual document, determining chemical data within the textual document, performing an analysis of the chemical data to identify a chemical pathway, and calculating a probability score for the chemical pathway.

Other aspects and embodiments of the present invention will become apparent from the following detailed description, which, when taken in conjunction with the drawings, illustrate by way of example the principles of the invention.

DETAILED DESCRIPTION

The following description discloses several preferred embodiments of systems, methods and computer program products for performing chemical textual analysis. Various embodiments provide a method to identify and analyze chemical terminology within textual data.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

The following description discloses several preferred embodiments of systems, methods and computer program products for performing chemical textual analysis.

In one general embodiment, a computer-implemented method includes identifying a textual document, determining chemical data within the textual document, performing an analysis of the chemical data to identify a chemical pathway, and calculating a probability score for the chemical pathway.

In another general embodiment, a computer program product for performing chemical textual analysis comprises a computer readable storage medium having program instructions embodied therewith, wherein the computer readable storage medium is not a transitory signal per se, and where the program instructions are executable by a processor to cause the processor to perform a method comprising identifying a textual document, utilizing the processor, determining chemical data within the textual document, utilizing the processor, performing an analysis of the chemical data to identify a chemical pathway, utilizing the processor, and calculating a probability score for the chemical pathway, utilizing the processor.

In another general embodiment, a system includes a processor and logic integrated with and/or executable by the processor, where he logic is configured to identify a textual document, determine chemical data within the textual document, perform an analysis of the chemical data to identify a chemical pathway, and calculate a probability score for the chemical pathway.

Figure 1:
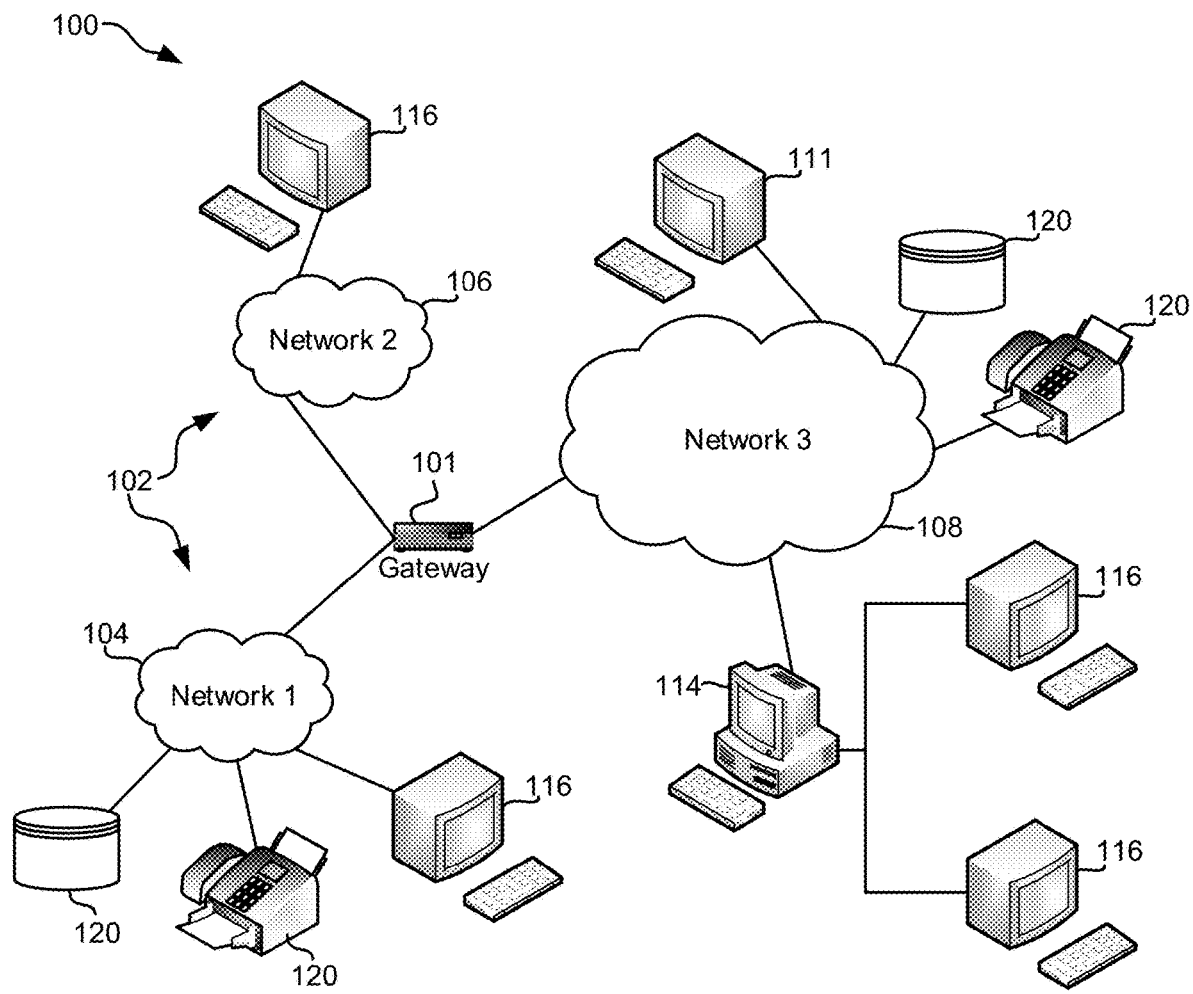
FIG. 1 illustrates a network architecture, in accordance with one embodiment.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
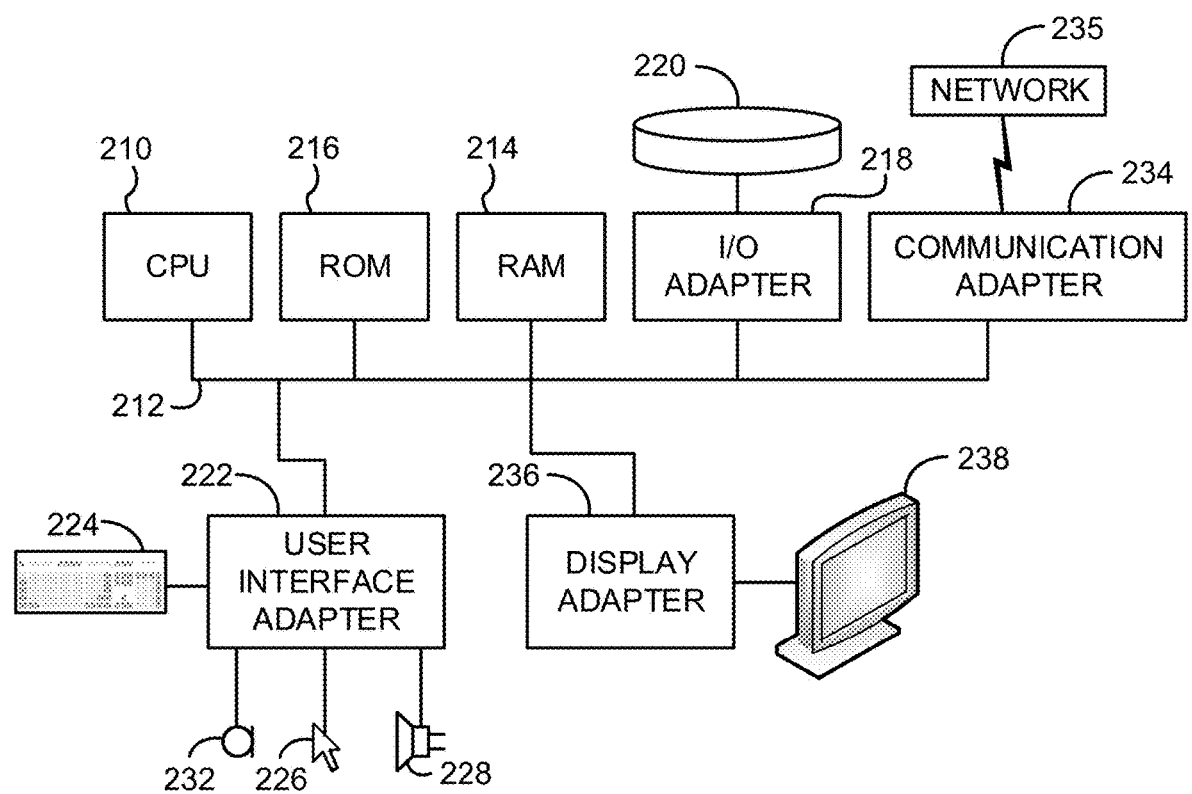
FIG. 2 shows a representative hardware environment that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

Figure 3:
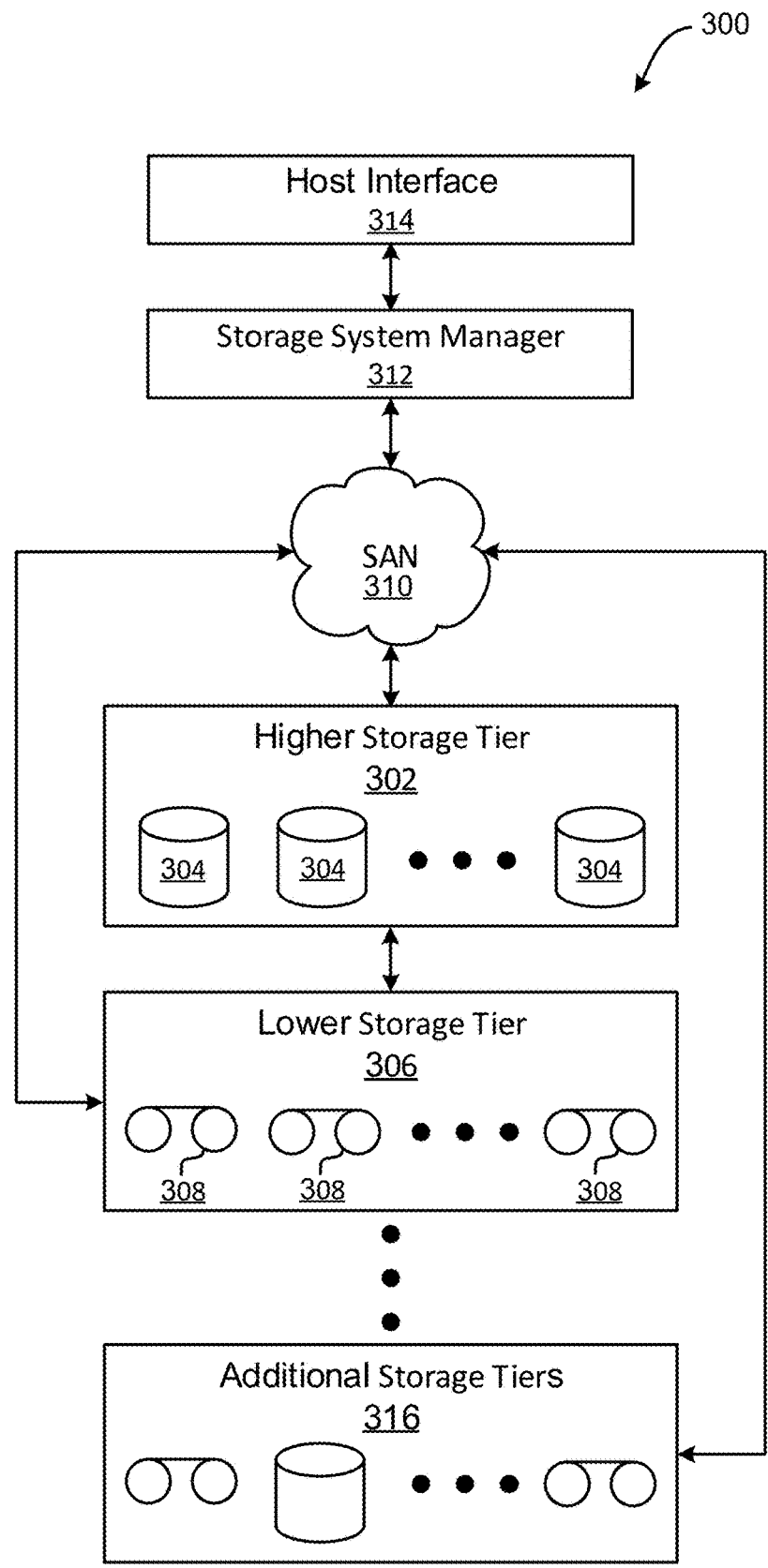
FIG. 3 illustrates a tiered data storage system in accordance with one embodiment.

Now referring to FIG. 3, a storage system 300 is shown according to one embodiment. Note that some of the elements shown in FIG. 3 may be implemented as hardware and/or software, according to various embodiments. The storage system 300 may include a storage system manager 312 for communicating with a plurality of media on at least one higher storage tier 302 and at least one lower storage tier 306. The higher storage tier(s) 302 preferably may include one or more random access and/or direct access media 304, such as hard disks in hard disk drives (HDDs), nonvolatile memory (NVM), solid state memory in solid state drives (SSDs), flash memory, SSD arrays, flash memory arrays, etc., and/or others noted herein or known in the art. The lower storage tier(s) 306 may preferably include one or more lower performing storage media 308, including sequential access media such as magnetic tape in tape drives and/or optical media, slower accessing HDDs, slower accessing SSDs, etc., and/or others noted herein or known in the art. One or more additional storage tiers 316 may include any combination of storage memory media as desired by a designer of the system 300. Also, any of the higher storage tiers 302 and/or the lower storage tiers 306 may include some combination of storage devices and/or storage media.

The storage system manager 312 may communicate with the storage media 304, 308 on the higher storage tier(s) 302 and lower storage tier(s) 306 through a network 310, such as a storage area network (SAN), as shown in FIG. 3, or some other suitable network type. The storage system manager 312 may also communicate with one or more host systems (not shown) through a host interface 314, which may or may not be a part of the storage system manager 312. The storage system manager 312 and/or any other component of the storage system 300 may be implemented in hardware and/or software, and may make use of a processor (not shown) for executing commands of a type known in the art, such as a central processing unit (CPU), a field programmable gate array (FPGA), an application specific integrated circuit (ASIC), etc. Of course, any arrangement of a storage system may be used, as will be apparent to those of skill in the art upon reading the present description.

In more embodiments, the storage system 300 may include any number of data storage tiers, and may include the same or different storage memory media within each storage tier. For example, each data storage tier may include the same type of storage memory media, such as HDDs, SSDs, sequential access media (tape in tape drives, optical disk in optical disk drives, etc.), direct access media (CD-ROM, DVD-ROM, etc.), or any combination of media storage types. In one such configuration, a higher storage tier 302, may include a majority of SSD storage media for storing data in a higher performing storage environment, and remaining storage tiers, including lower storage tier 306 and additional storage tiers 316 may include any combination of SSDs, HDDs, tape drives, etc., for storing data in a lower performing storage environment. In this way, more frequently accessed data, data having a higher priority, data needing to be accessed more quickly, etc., may be stored to the higher storage tier 302, while data not having one of these attributes may be stored to the additional storage tiers 316, including lower storage tier 306. Of course, one of skill in the art, upon reading the present descriptions, may devise many other combinations of storage media types to implement into different storage schemes, according to the embodiments presented herein.

According to some embodiments, the storage system (such as 300) may include logic configured to receive a request to open a data set, logic configured to determine if the requested data set is stored to a lower storage tier 306 of a tiered data storage system 300 in multiple associated portions, logic configured to move each associated portion of the requested data set to a higher storage tier 302 of the tiered data storage system 300, and logic configured to assemble the requested data set on the higher storage tier 302 of the tiered data storage system 300 from the associated portions.

Of course, this logic may be implemented as a method on any device and/or system or as a computer program product, according to various embodiments.

Figure 4:
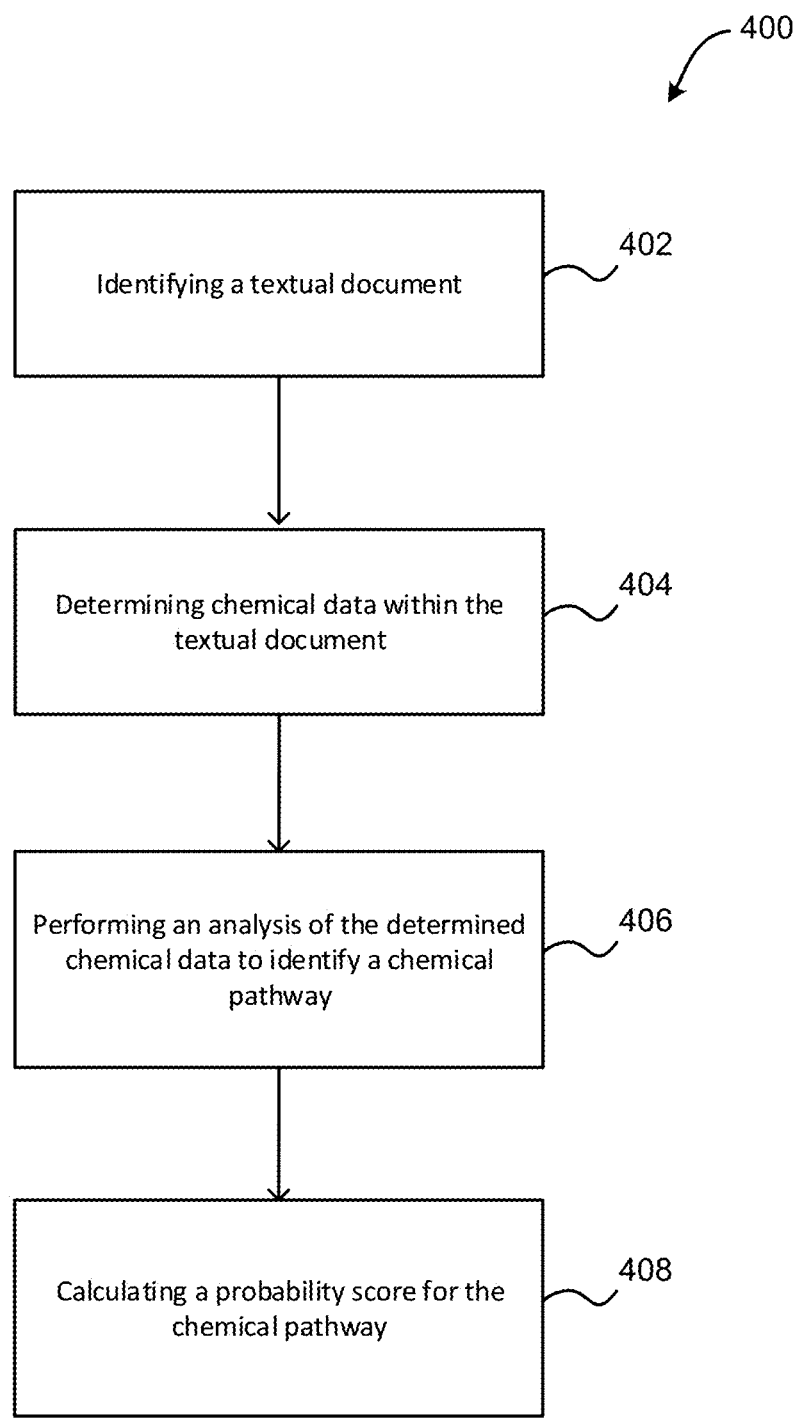
FIG. 4 illustrates a method for performing chemical textual analysis, in accordance with one embodiment.

Now referring to FIG. 4, a flowchart of a method 400 is shown according to one embodiment. The method 400 may be performed in accordance with the present invention in any of the environments depicted in FIGS. 1-3 and 5-6, among others, in various embodiments. Of course, more or less operations than those specifically described in FIG. 4 may be included in method 400, as would be understood by one of skill in the art upon reading the present descriptions.

Each of the steps of the method 400 may be performed by any suitable component of the operating environment. For example, in various embodiments, the method 400 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 4, method 400 may initiate with operation 402, where a textual document is identified. In one embodiment, the textual document may include a document written in a natural language using alphanumerical text. In another embodiment, the textual document may be included within a plurality of documents (e.g., a corpus of documents, an index of documents, etc.). In yet another embodiment, the textual document may include one or more of a research paper, a publication, a textbook, a blog post, a web page, etc.

In still another embodiment, the textual document may include text associated with the field of chemistry. For example, the textual document may include text that describes one or more chemical components (e.g., one or more chemicals, compounds, molecules, etc.), chemical reactions, chemical products, chemical byproducts, etc. In another embodiment, the textual document may describe one or more experiments, one or more results of the experiments, etc. In yet another embodiment, the textual document may describe one or more known chemical reactions.

Additionally, in one embodiment, the textual document may be retrieved from a document database (e.g., a hardware database, a virtual database, a cloud-based database, etc.). In another embodiment, the textual document may be created by scanning printed text and converting the text to a digital form using an optical character recognition (OCR) application. In yet another embodiment, the textual document may be submitted by a user. In still another embodiment, the textual document may be identified by a computing device (e.g., a computer, a server, a cloud computing device, a mobile computing device, etc.). For example, the textual document may be identified as a result of the computing device performing data retrieval (e.g., by crawling one or more databases and/or one or more networks, etc.).

Further, as shown in FIG. 4, method 400 may proceed with operation 404, where chemical data is determined within the textual document. In one embodiment, determining the chemical data may include analyzing the textual document. For example, analyzing the textual document may include parsing the textual document, identifying components of the textual document, extracting information from the textual document, etc.

In another embodiment, analyzing the textual document may include analyzing one or more relationships between a plurality of terms found in the textual document. For example, analyzing the textual document may include identifying one or more relationships between words within the textual document. For instance, the relationships between words within the textual document may indicate one or more relationships between one or more chemical components (e.g., one or more chemicals, compounds, molecules, solvents, etc.).

Further still, in one embodiment, one or more applications may be utilized during the analyzing of the textual document. For example, cheminformatics software (e.g., RDKit, etc.) may be used to translate textual strings into chemical components such as molecules in a standardized manner. In another example, the cheminformatics software may be used to translate information such as chemical and reaction information (e.g., properties, kinetics, etc.) to and from structural and textual embodiments.

Also, in one embodiment, determining chemical data within the textual document may include determining data associated with a plurality of chemical components (e.g., chemicals, compounds molecules, etc.). In another embodiment, the data may include data indicating a structure (e.g., molecular structure, etc.). For example, the determined chemical data may include bond order (e.g., single bonds, double bonds, triple bonds, etc.), the aromaticity of a molecule, a ring structure of a molecule, etc. In another embodiment, the chemical data may include a description of a molecular bond. For example, the chemical data may include an indication as to whether the molecular structure has unbound electrons that would allow for additional reactivity, etc.

In addition, in one embodiment, the determined chemical data may include an indication of reactiveness (e.g., of a molecule, an element, etc.). For example, the determined chemical data may include the aromaticity of a molecule, which may suggest a reactiveness of the molecule. In another example, the determined chemical data may include a hydration/aqueousness of a molecule, which may suggest a reactiveness of the molecule.

Furthermore, in one embodiment, the determined chemical data may include an analysis of a chemical reaction included within the textual document, including one or more extracted details of a chemical reaction. For example, the determined chemical data may include an indication and details of precipitation/precipitates, an indication and details of an acid/base reaction, an indication and details of oxidation, an indication and details of hydration/aqueousness, an indication and details of solubility, etc. In another example, the determined chemical data may include an indication and details of a relationship between one or more reagents, one or more reactants, and products of the chemical reaction. In yet another example, the determined chemical data may include a description of one or more type of bonds existing before the chemical reaction, formed by the chemical reaction, etc.

Further still, analyzing the textual document may include identifying one or more chemical variables within the textual document. For example, analyzing the textual document may include identifying one or more reactions, elements, compounds, molecules, solvents, etc.

Further still, as shown in FIG. 4, method 400 may proceed with operation 406, where an analysis of the determined chemical data is performed to identify a chemical pathway. In one embodiment, the chemical pathway may include an identification of a chemical reaction. For example, the chemical pathway may include an identification of a plurality of steps involved in the chemical reaction. In another embodiment, the chemical pathway may include an identification of one or more components of a chemical reaction. For example, the chemical pathway may include an identification of one or more reactants in the reaction, one or more characteristics of the reaction itself, one or more byproducts of the chemical reaction, etc. In yet another embodiment, the chemical pathway may include one of a plurality of possible outcomes of a chemical reaction. In still another embodiment, the chemical pathway may include one of a plurality of configurations of one or more molecules (e.g., molecules involved in the chemical reaction, etc.).

Also, on one embodiment, performing the analysis may include identifying one or more chemical components and/or reactions within the textual document and determining one or more characteristics of one or more chemical components and/or reactions identified within the textual document. For example, performing the analysis may include determining for a chemical component a number and type of atoms of the component, the aromaticity of the component, a reactivity of the component, the kinetic energy of a reaction, the activation energy of a reaction, etc.

Additionally, in one embodiment, performing the analysis of the determined chemical data may include assigning one or more scores to each of the determined characteristics of the one or more chemical components and/or reactions. For example, the scores may include metadata associated with a chemical component and/or reaction. In another example, each of the scores may be based on an analysis of one or more factors associated with the chemical component and/or reaction.

For instance, reactiveness characteristics of a chemical component, such as aromaticitiy and aqueousness, and previous successful reactions involving the chemical components may be analyzed to determine a reactiveness score that may be stored as metadata in association with a chemical component. In another example, scores of various characteristics may be used to determine a number of hydrogen atoms of a component, a reactivity of the component, the kinetic energy of the reaction, an activation energy of the reaction, etc.

Further, in one embodiment, the scores may be determined utilizing an analysis of data associated with a plurality of chemical components. For example, predetermined rules and/or cheminformatics software may be used to analyze the data and determine associated scores. In another embodiment, performing the analysis may include identifying one or more starting components of a chemical reaction as well as one or more steps of one or more pathways that occur during the chemical reaction.

Further still, in one embodiment, performing the analysis may include identifying and/or predicting one or more chemical components having similar characteristics (e.g., anti-viral characteristics, etc.) to a chemical component found within the textual document. In another embodiment, performing the analysis may include analyzing one or more chemical components within the textual document to determine one or more patterns. In yet another embodiment, performing the analysis may include visually reproducing one or more of the chemical components found within the textual document. For example, one or more molecules may be graphed (e.g., using one or more applications) and relationships between molecules, edges, etc. may be determined and illustrated visually.

Also, as shown in FIG. 4, method 400 may proceed with operation 408, where a probability score is calculated for the chemical pathway. In one embodiment, the probability score for the chemical pathway may include a probability of one or more outcomes associated with one or more identified chemical components, one or more scenarios, etc.

In one embodiment, calculating the probability score may include predicting one or more outcomes associated with one or more identified chemical components, one or more scenarios, etc. For example, a probability of a reaction occurring between one or more identified chemical components may be determined. In another embodiment, one or more probable results of the reaction between the one or more chemical components may be determined. In another embodiment, calculating the probability score may include predicting a viability of one or more reactions that include one or more identified chemical components.

For example, each individual chemical component may have one or more associated individual scores/weights, and such weights may be combined for groups of chemical components and may be compared to predetermined thresholds to determine whether the groups of chemical components will react. In another example, one or more outcomes for one or more reactions involving the identified chemical components may be determined.

In addition, in one embodiment, calculating the probability score may utilize one or more supplements. For example, one or more applications may be used to predict outcomes, identify components, etc. For instance, for outcome prediction, determined chemical data may be analyzed using known information via an application (e.g., RDKit, etc.), which may build a predictive model of whether a reaction is viable. In another example, the application may provide molecular properties and may translate the properties into a form (e.g., an annotated form, etc.) that may be used to score certain features. In yet another example, a knowledge base containing one or more known characteristics of chemical components, one or more known results of chemical reactions, etc. may be used to predict outcomes, identify components, etc.

In another embodiment, information may be added to the knowledge base based on the results of the analysis and the calculated probability score. For example, predicted outcomes, identified components, etc. may be added to an existing knowledge base to be used for future determination and analysis in association with additional textual documents.

In this way, results of an identification and analysis of chemical components and reactions within a textual document may build a comprehensive knowledge base of components and reactions and may utilize calculated metadata associated with the components and reactions (e.g., prediction, probability of success, reactivity of products, etc.) to minimize real-world experimentation required to determine viability of chemical pathways, results of chemical reactions, determination of similar components, etc.

Additionally, in one embodiment, a chemistry-based analysis of molecules may be performed, which may be used to build predictive models, predict chemical reactions and pathways, and to figure out how to build molecules that have not been previously synthesized. Additionally, a number of synthesis steps may be reduced during a chemical synthesis process (e.g., from X to X-Y). Further, one or more known chemical and/or kinetic reactions present in the textual document may be identified and learned.

Further, in one embodiment, a molecule/compound may be identified that has not been synthesized, and the main components of the compound may be determined. In another embodiment, a model may be trained based on one or more chemical reactions and then a projection and prediction may be performed based on the model.

Figure 5:
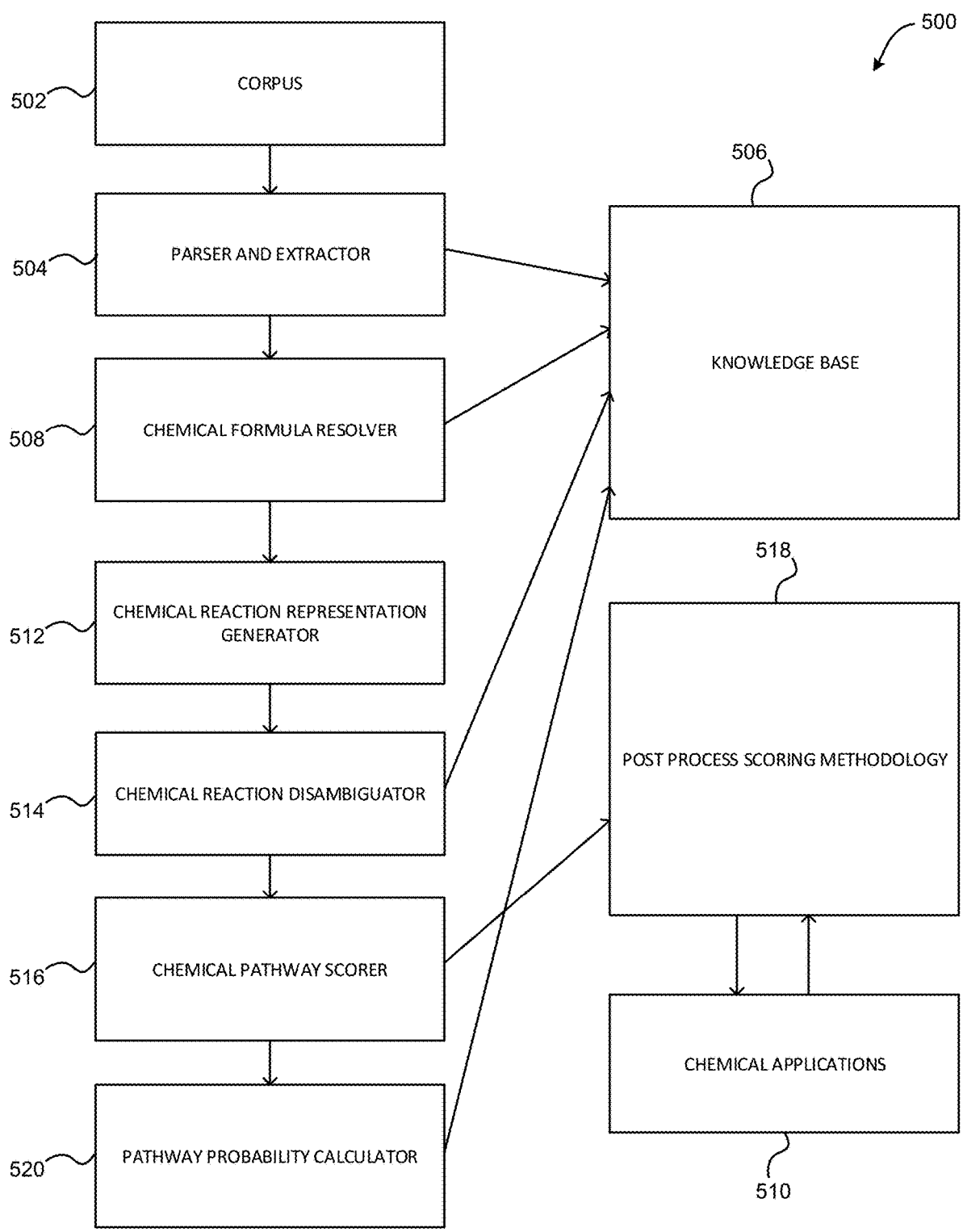
FIG. 5 illustrates an exemplary chemical pathway discovery environment, in accordance with one embodiment.

FIG. 5 illustrates an exemplary chemical pathway discovery environment 500, in accordance with one embodiment. As shown in FIG. 5, the environment 500 includes a parser and extractor 504 that retrieves textual data from a corpus 502. In one embodiment, the corpus 502 includes one or more of literature, texts, web content, scanned content, etc. In another embodiment, the parser and extractor 504 parses one or more textual elements within the corpus 502. In yet another embodiment, the parser and extractor 504 identifies and retrieves a relationship between textual data within the corpus 502.

Additionally, the parser and extractor 504 is in communication with a knowledge base 506. In one embodiment, the knowledge base 506 may include a listing of a plurality of chemical concepts. For example, the knowledge base 506 may include an identification and description of all known periodic elements, all known common compounds, all known metabolic pathways, all known chemical and molecular properties, all known chemical pathway relationships, all known chemical targets, etc. In another embodiment, the parser and extractor 504 may use the knowledge base 506 to assist in the extraction of textual data from the corpus 502 (e.g., help convert extracted data to a standardized format, etc.). In yet another embodiment, the parser and extractor 504 may convert an identified molecule in the corpus to text.

Further, the results of the parser and extractor 504 (e.g., the parsed and extracted textual data, etc.) are sent to a chemical formula resolver 508 that is also in communication with the knowledge base 506 as well as chemical applications 510. In one embodiment, the chemical formula resolver 508 may access the knowledge base 506 to verify the parsed and extracted textual data. For example, the chemical formula resolver 508 may access the knowledge base 506 to determine whether the components of the parsed and extracted textual data are chemically correct.

Further still, in one embodiment, the chemical formula resolver 508 may access the knowledge base 506 and the chemical applications 510 to determine a validity of the parsed and extracted textual data (e.g., does the data make sense, have the results been seen before in literature, etc.). In another embodiment, the chemical formula resolver 508 may identify and resolve/correct errors (e.g., typographical errors, logical errors, etc.) within the parsed and extracted textual data, utilizing information stored within the knowledge base 506. In yet another embodiment, the knowledge base 506 may be updated with one or more analysis results, such that the knowledge base 506 may dynamically expand.

Also, the results of the chemical formula resolver 508 are sent to the chemical reaction representation generator 512. In one embodiment, the results of the chemical formula resolver 508 may include extracted textual data that has been resolved and formatted to a standardized format. In another embodiment, the chemical reaction representation generator 512 may then create a representation of a chemical reaction based on the received resolved and formatted data. For example, the representation of the chemical reaction may include an indication of one or more reagents of the chemical reaction, one or more chemical reactions, one or more products of the chemical reaction, etc.

In addition, in one embodiment, only a portion of a chemical reaction equation may be provided by the chemical formula resolver 508, and the chemical reaction representation generator 512 may enumerate one or more possible reactions, one or more possible results, or one or more possible equations from the given portion.

Furthermore, the results of the chemical reaction representation generator 512 (e.g., a formatted representation of a chemical reaction, etc.) are sent to a chemical reaction disambiguator 514 that is also in communication with the knowledge base 506. In one embodiment, the chemical reaction disambiguator 514 may review, verify, and validate the representation of a chemical reaction, based on known chemical reactions, known compounds, and known chemical and molecular properties found in the knowledge base 506. For example, the chemical reaction disambiguator 514 may review chemical pathways already identified from within the corpus 502 stored in the knowledge base 506 and may compare those pathways to one or more molecules that are associated with the chemical reaction to confirm the validity of the chemical reaction.

Further still, the results of the chemical reaction disambiguator 514 (e.g., a verified and formatted representation of a chemical reaction, etc.) are sent to a chemical pathway scorer 516 that applies a post process scoring methodology 518 to the representation of the chemical reaction. In one embodiment, the post process scoring methodology 518 may include a plurality of criteria that influence a score determined for a plurality of elements within the representation of the chemical reaction. For example, the criteria within the post process scoring methodology 518 may include one or more of a chemical similarity check and associated scoring, a stoichiometry check, an aromatic scoring, a bonds and solubility scoring, a reaction type tendency scoring, etc. In another example, each of the criteria may be compared against the representation of the chemical reaction to determine an individual score associated with that specific pathway, which may be stored or combined with other scores associated with other criteria.

Also, the post process scoring methodology 518 is linked to the chemical applications 510. In one embodiment, the chemical applications 510 may include one or more applications that assist with verifying one or more chemical elements, determining certain elements like aromaticity, bonds, reaction types, etc. In this way, the chemical applications may help the chemical pathway scorer 516 implement the scoring methodology 518. In another embodiment, the chemical applications may include one or more of Tversky, Fraggle, RDKit, etc.

Additionally, the results of the chemical pathway scorer 516 (e.g., a scored, verified, and formatted representation of a chemical reaction, etc.) is sent to the pathway probability calculator 520. In one embodiment, the pathway probability calculator 520 may determine a probability of a successful chemical reaction, given the scores computed by the chemical pathway scorer 516. In another embodiment, the pathway probability calculator 520 may determine a probability that there will be a viable chemical pathway corresponding to the received representation.

Further, the pathway probability calculator 520 is linked to the knowledge base 506. In one embodiment, the pathway probability calculator 520 may identify one or more known chemical targets within the knowledge base 506 and may compare the known chemical targets to the received representation of the chemical reaction to determine whether the pathway indicated by the received representation is a viable pathway to try to achieve (e.g., via experimentation, etc.).

In one embodiment, the determination of a viable pathway may utilize the stoichiometry of the chemical reaction, including the solubility, the reaction tendency of the reactants, and the similarity score to a target molecule proportional to the aromatic score and bond type score of the reactants. For example, $S_1$ may represent a solubility score, $t_1$ may represent a reaction tendency score, $c_1$ may represent a corpus tendency score, $l_1$ may represent a similarity score, $r_1$ may represent a similarity reference score, $a_1$ may represent an aromaticity score, and $b_1$ may represent a bond type score.

In another example, the solubility score may include a normalized value of the solubility of the molecule at a specific temperature and atmospheric pressure in 100 ML of the solvent. The value may include an amount of the compound required. For example, $BaCl_2$ may have a solubility score at 0.358 based on its solubility of 35.8 g/100 mL at 20 degrees Celsius in water. In another embodiment, the reaction tendency score may include the chemical affinity score if one can be found from a lookup table; otherwise it may be a number of bond acceptors or donors the molecule contains (e.g., hydrogen-bond donors (h-bond donors), etc.).

Additionally, in one embodiment, a corpus tendency may include a number of passages found with the same type of chemical reaction normalized by the total number of passages in the documents parsed. In another embodiment, a similarity score may include the Tversky score for the molecule, and the similarity reference score may include a number of passages with the same or similar compounds in the corpus normalized to the total number of passages in the corpus.

Further, in one embodiment, a bond type scores may include point scores, for example, 25 points for single bonds, 40 points for double bonds and 60 points for triple bond compounds. The aromatic score may include 1 point if not applicable; however, if applicable, it may include 10 points for each aromatic feature shape, ring, bonds, planar and delocalized electrons. A representative probability score computation equation may include a sum of the scores for each molecule that is a reagent in the equation, or using LaTeX Mathematical equations Probability Score=\sum_{i=1}^{n}\frac{S_i+(t_i*c_i)+(l_i*r_i))}{(a_i+b_i)}.

Table 1 illustrates an exemplary equation that calculates the probability score as a sum of the scores for each molecule that is a reagent in the equation. Of course, it should be noted that the exemplary equation shown in Table 1 is set forth for illustrative purposes only, and thus should not be construed as limiting in any manner.

TABLE 1

$$\text{Probability Score} = \sum_{i=1}^{n} \frac{S_i + (t_i * c_i) + (l_i * r_i))}{(a_i + b_i)}$$

Figure 6:
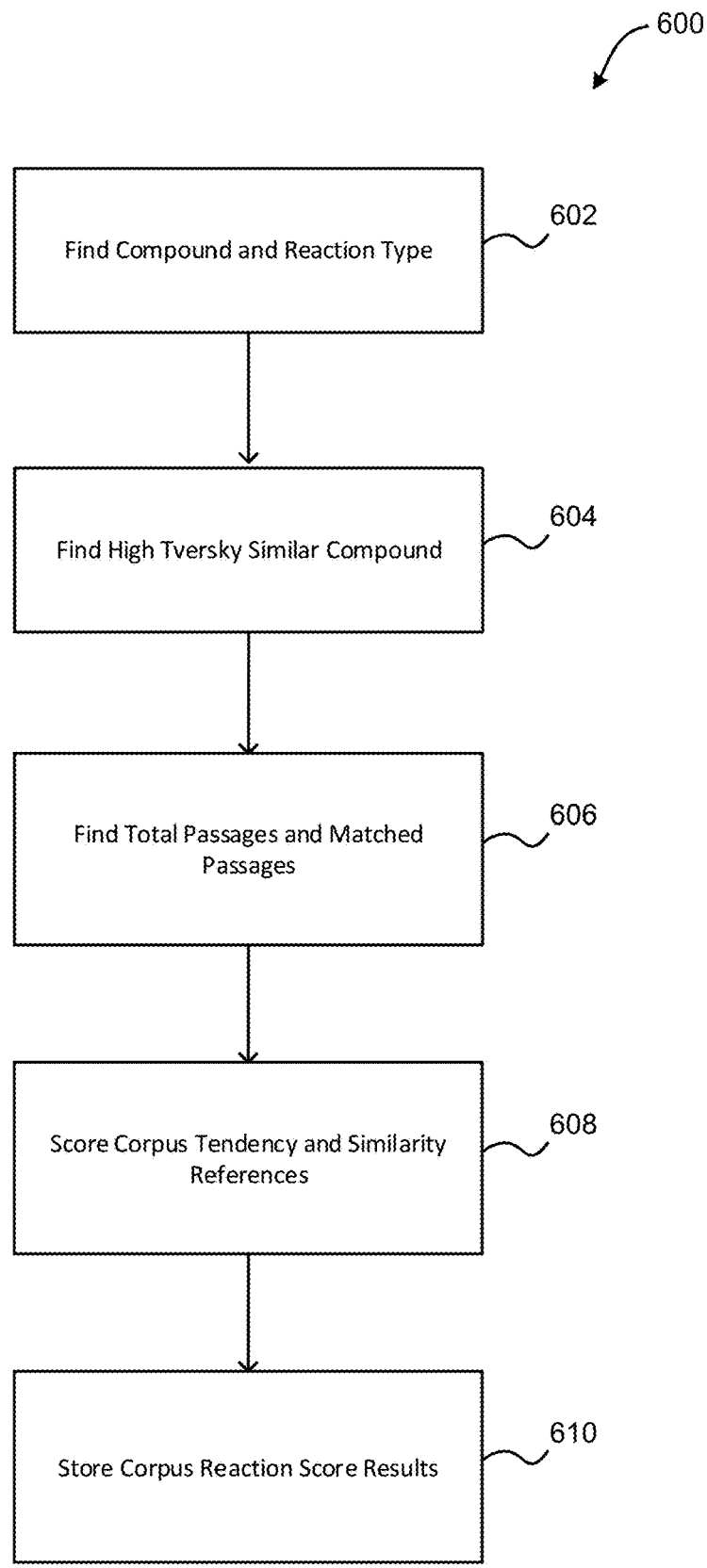
FIG. 6 illustrates a method for performing reaction corpus scoring, in accordance with one embodiment.

Now referring to FIG. 6, a flowchart of a method 600 for performing reaction corpus scoring is shown according to one embodiment. The method 600 may be performed in accordance with the present invention in any of the environments depicted in FIGS. 1-5, among others, in various embodiments. Of course, more or less operations than those specifically described in FIG. 6 may be included in method 600, as would be understood by one of skill in the art upon reading the present descriptions.

Each of the steps of the method 600 may be performed by any suitable component of the operating environment. For example, in various embodiments, the method 600 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 600. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 6, method 600 may initiate with operation 602, where the reaction corpus scoring retrieves a compound with similar reaction types from one or more passages in the corpora being used. In one embodiment, the reaction types may include melting, sublimation, evaporation, and condensation, oxidation, precipitation, etc. Additionally, method 600 may proceed with operation 604, where similar compounds with a high Tversky similarity score to the compound reactant are searched, found, and counted.

Further, method 600 may proceed with operation 606, where a total number of passages that matched in similarity or reaction type during the search for similar compounds is noted. In one embodiment, one or more of operations 602-606 may utilize reaction and compound passage data stored in a shared database.

Further still, method 600 may proceed with operation 608, where the corpus tendency score is calculated by multiplying an affinity or the h-bond donors or acceptors in the compound by the number of matched passages divided by the total number of passages. In another embodiment, the similarity reference score may include matched similar compound passages that are over a Tversky threshold value and that are divided by the total number of passages. In one embodiment, one or more of operations 606-608 may utilize the retrieved Tversky threshold stored in a shared database. Also, method 600 may proceed with operation 610, where the corpus tendency and similarity scores are stored in a corpus reaction database for use.

In this way, a pathway probability calculator may determine whether an experiment itself is viable and whether the experiment is it going to react the way it is intended, based on an analysis of corpus textual data. Also, one or more outcomes of the experiment may be predicted, based on the analysis.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:
1. A computer-implemented method, comprising:
 identifying a textual document, utilizing a processor;

identifying a chemical pathway including a plurality of chemical components within the textual document, utilizing the processor;

combining individual associated weights of each of the plurality of chemical components utilizing the processor;

comparing, utilizing the processor, the combined weights to a predetermined threshold to determine whether the plurality of chemical components will react; and training, utilizing the processor, a predictive model based on the determination as to whether the plurality of chemical components will react.

2. The computer-implemented method of claim 1, comprising:

performing, utilizing the processor, a prediction utilizing the predictive model.

3. The computer-implemented method of claim 1, comprising converting text within the textual document to a digital form, utilizing optical character recognition (OCR).

4. The computer-implemented method of claim 1, comprising translating textual strings within the textual document into the plurality of chemical components, utilizing cheminformatics software.

5. The computer-implemented method of claim 1, comprising saving the determination as to whether the plurality of chemical components will react in association with the chemical components within a knowledge base as one of a plurality of possible outcomes of a reaction.

6. The computer-implemented method of claim 1, wherein the textual document is retrieved by crawling one or more databases.

7. The computer-implemented method of claim 1, comprising identifying one or more patterns within one or more of the chemical components identified within the textual document.

8. The computer-implemented method of claim 1, comprising predicting an outcome of a chemical reaction, utilizing the plurality of chemical components.

9. The computer-implemented method of claim 1, comprising comparing one or more of the plurality of chemical components to a knowledge base to determine one or more characteristics of the chemical components.

* * * * *